United States Patent
Giori et al.

(10) Patent No.: US 6,818,761 B2
(45) Date of Patent: Nov. 16, 2004

(54) POLYSACCHARIDE OF *ECHINACEA ANGUSTIFOLIA*

(75) Inventors: Andrea Giori, Milan (IT); Alessandro Anelli, Milan (IT); Paolo Morazzoni, Milan (IT); Francesco Di Pierro, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/302,843

(22) Filed: Nov. 25, 2002

(65) Prior Publication Data

US 2004/0024199 A1 Feb. 5, 2004

(30) Foreign Application Priority Data

Jul. 30, 2002 (IT) ...................................... MI2002A1692

(51) Int. Cl.$^7$ ........................ C08B 37/00; A61K 31/715
(52) U.S. Cl. .................... 536/123; 536/123.1; 536/124; 514/23; 514/54
(58) Field of Search .............................. 536/123.1, 124; 514/23

(56) References Cited

U.S. PATENT DOCUMENTS 4,857,512 A  *  8/1989  Wagner et al. ................ 514/54

FOREIGN PATENT DOCUMENTS

WO    WO 01/22977    *    5/2001    .......... A61K/35/00

OTHER PUBLICATIONS

Bukovsky, M. et al., "Immunomodulating Activity of *Echinacea Gloriosa* L., *Echinacea Angustifolia* DC and *Rudbeckia Speciosa* Wenderoth Ethanol–Water Extracts", *Polish Journal of Pharmacology*, Institute of Pharmacology, Krakow, vol. 47, No. 2, 1995, pp. 175–177.

E. Tragni et al., "Evidence From Two Classic Irritation Tests for an Anti–flammatory Action of a Natural Extract, Echinacina B", *Food Chem. Toxicol.*, vol. 23, 1985, pp. 317–319.

Rudolf Bauer et al., "Alkamides from the Roots of *Enchinacea Angustifolia*," Phytochemistry, V. 28, 1989, pp. 505–508.

R. Bauer et al., "TLC and HPLC Analysis of Alkamides in *Echinacea* Drugs," Planta Medica, V. 55, 1989, pp. 367–371.

* cited by examiner

*Primary Examiner*—James O. Wilson
*Assistant Examiner*—Ganapathy Krishnan
(74) *Attorney, Agent, or Firm*—Young & Thompson

(57) ABSTRACT

A polysaccharide of *Echinacea angustifolia* roots, having molecular weight of $1.3 \times 10^5$ Da and including rhamnose, arabinose, galactose and galacturonic acid in ratio 0.5:2.5:1.75:10.25, is recovered from spontaneous or cultivated *Echinacea angustifolia* roots by means process including the following steps: a) depriving the roots of non polysaccharidic constituents by extraction with solvent; b) extracting the polysaccharidic fraction from the roots as directly obtained from the preceding step; c) isolating the polysaccharide by chromatography of the polysaccharidic fraction. Due to its immune-stimulating properties, the polysaccharide can be used for the preparation of medicaments, food supplements or nutraceutical compositions to administer whenever it is desirable to strenghthen the immune system body defenses.

20 Claims, 3 Drawing Sheets

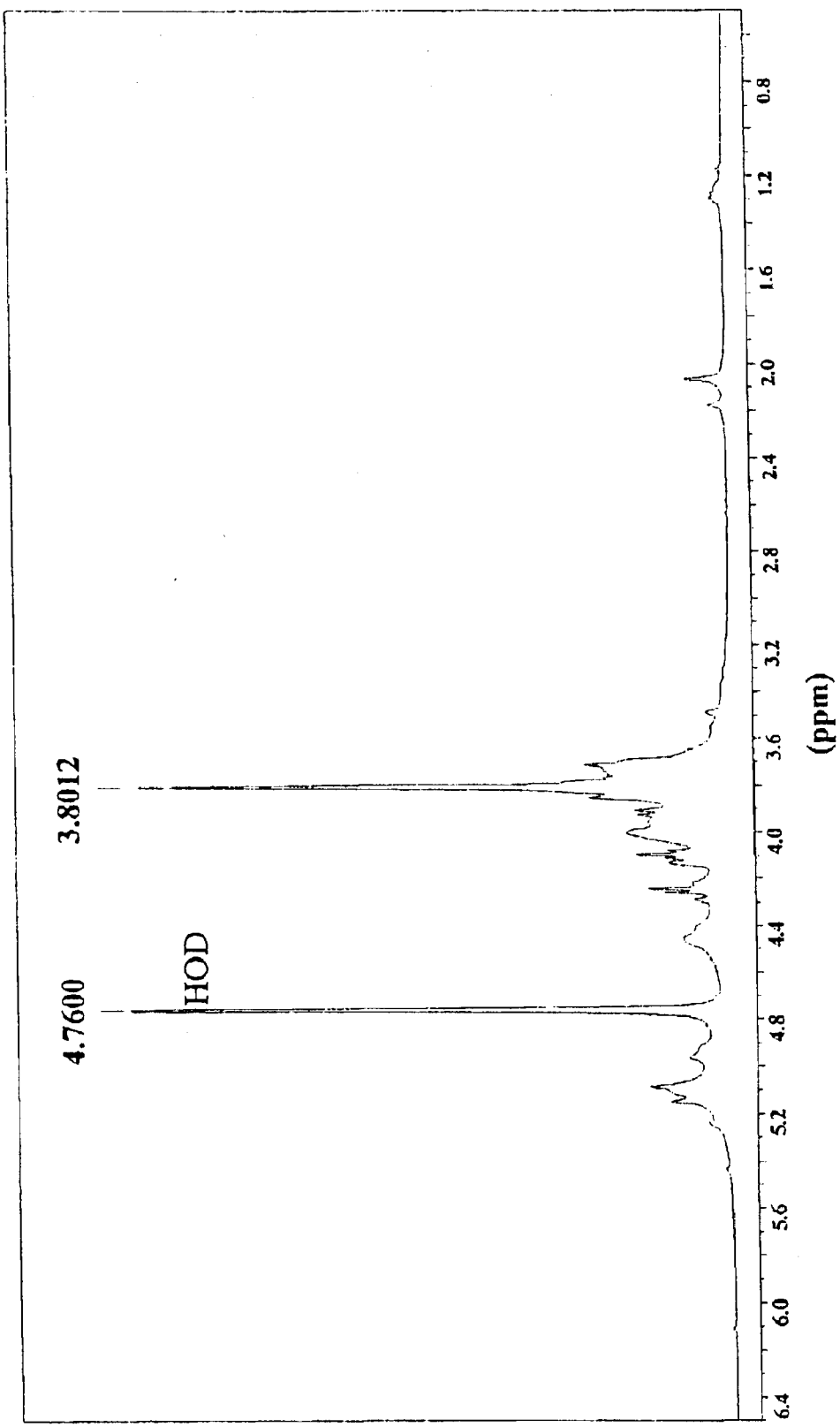
Figure 1: 1H NMR spectrum of the polysaccharide 1

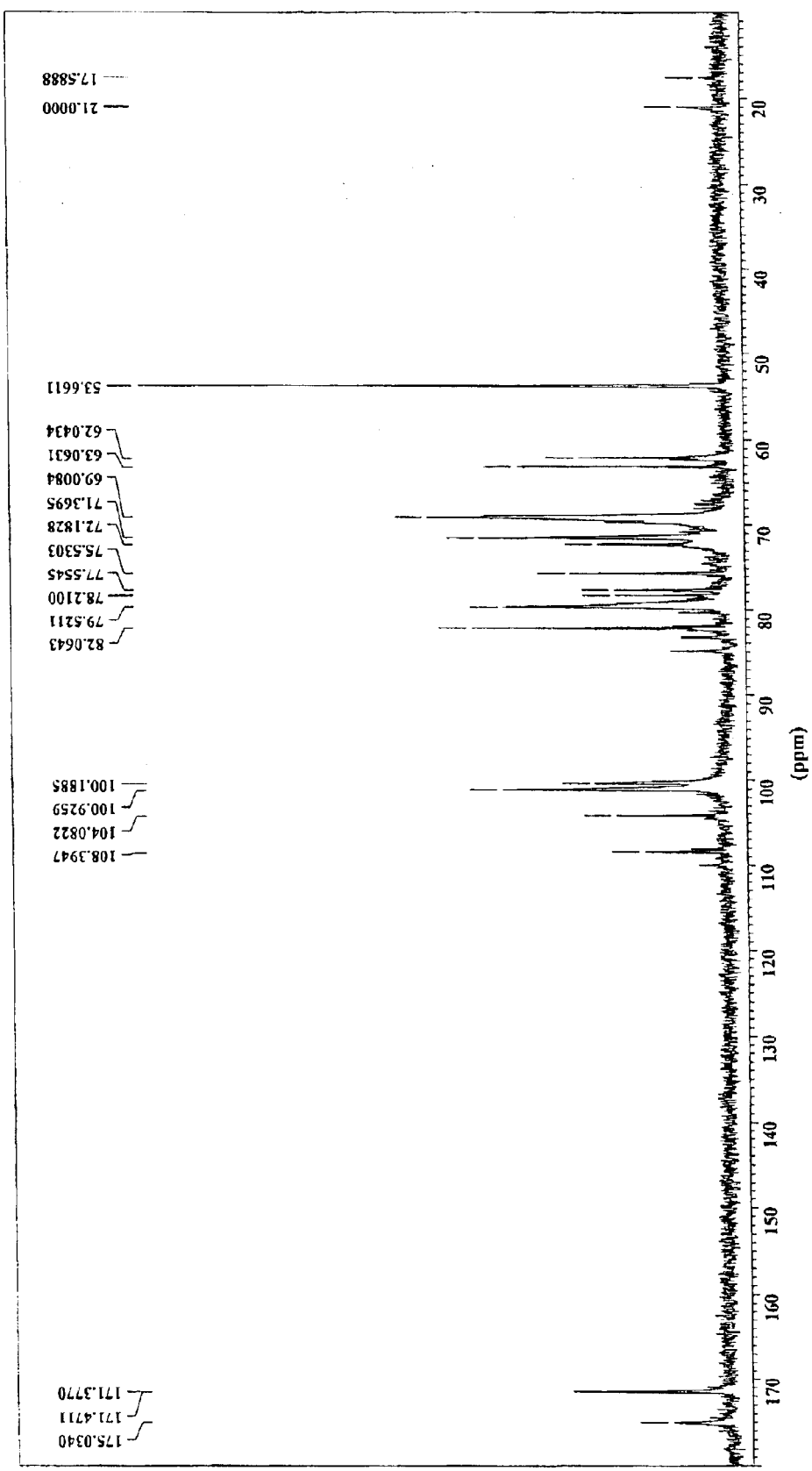
Figure 2: 13C NMR spectrum of the polysaccharide 1

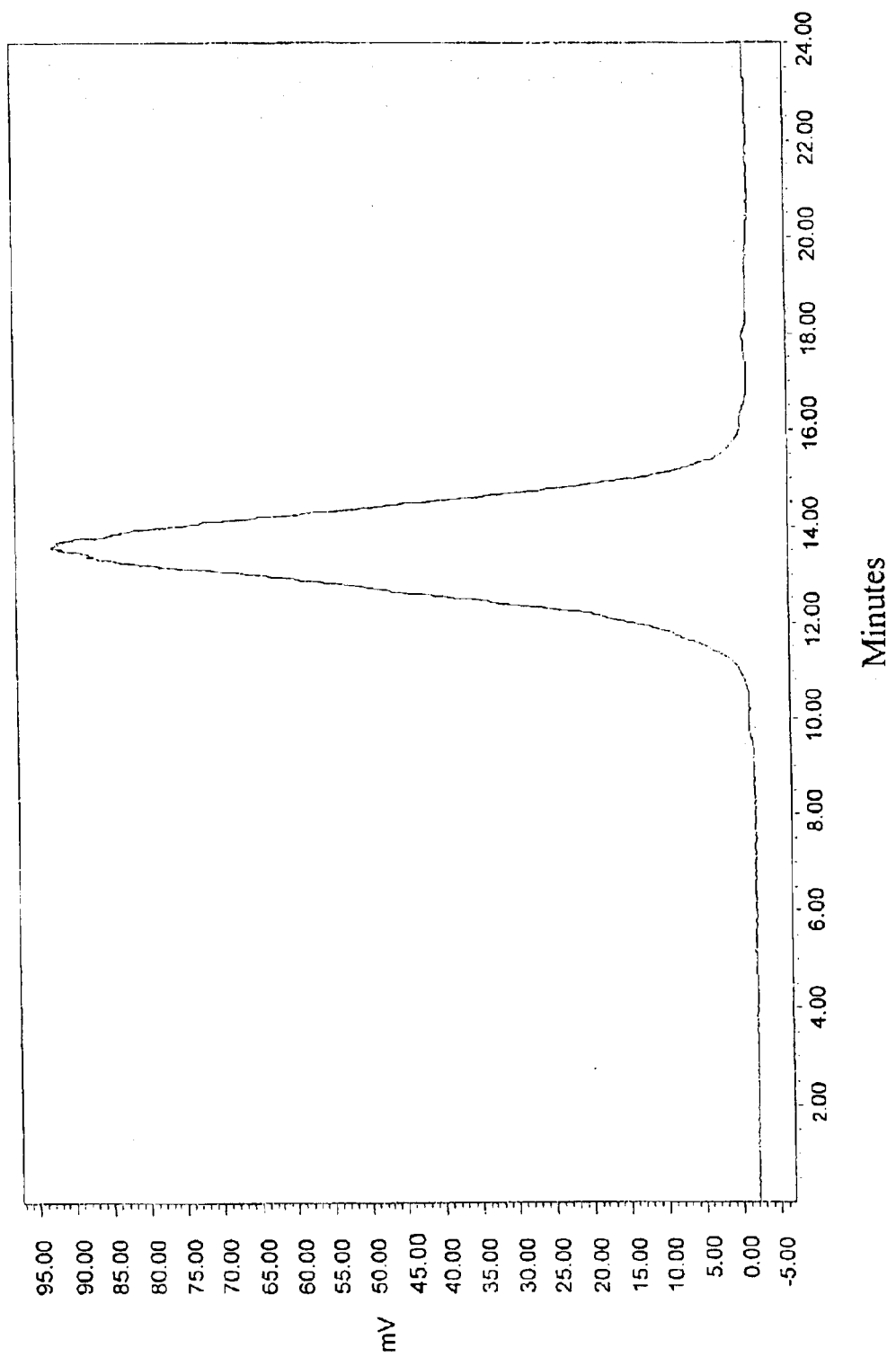
Figure 3: GPC profile of the polysaccharide 1

POLYSACCHARIDE OF ECHINACEA ANGUSTIFOLIA

FIELD OF THE INVENTION

The present invention relates to the field of polysaccharides, in particular to a polysaccharide of *Echinacea angustifolia* and to a process for the preparation thereof. The polysaccharide can be used in the treatment of pathological conditions in which it is desirable to strengthen the immune defenses.

BACKGROUND OF THE INVENTION

*Echinacea* is a plant which originates from North America and Mexico; its therapeutical properties were well known to native Americans, who used it for healing wounds. Due to the fact that *Echinacea* was deemed able to increase the resistance to infections, during the first years of the last century its use in the treatment of local and generalised infections became widespread. *Echinacea*, in particular *Echinacea angustifolia*, is nowadays highly recommended for the treatment of influenza syndromes and in particular for the treatment of cold, for healing wounds and for the treatment of mycosis.

The general action is apparently due to the aspecific stimulation of the immune system and to the sensitisation of germs and pathogens to chemotherapeutics and antibiotics. The cicatrizing properties seem ascribable to the capacity of stabilizing hyaluronic acids through of hyaluronidase inhibition exerted by one of the active principles contained in the plant, i.e. echinacoside, and to the massive macrophages activation induced by polysaccharides. In this way any foci of infection remain localised and accumulation of mucopolysaccharides and hystoplastic material necessary for reparative processes is favoured.

As a large fraction of *Echinacea* polysaccharides consists of inulin, which cannot be deemed responsible for the above cited properties, there is the need to identify the active polysaccharide and to provide an effective process for the extraction and purification thereof.

DETAILED DISCLOSURE OF THE INVENTION

Object of the present invention is a polysaccharide from *Echinacea angustifolia* roots (hereinafter referred to as "the polysaccharide"), having molecular weight of $1.3 \times 10^5$ Da and consisting of rhamnose, arabinose, galactose and galacturonic acid in 0.5:2.5:1.75:10.25 ratio. In the skeleton of the polysaccharide, straight and branched portions alternate, the straight portions consisting of partially acetylated (9%) and methylated (35%) galacturonic acid residues linked via α-(1–4) bond and the branched portions consisting of an alternation of galacturonic acid and rhamnose, to which side chains containing arabinose and galactose in 2.5:1.75 ratio are attached. The polysaccharide is characterized by $^1$H-NMR, $^{13}$C-NMR spectra and GCP profile as reported in FIGS. 1–3.

The polysaccharide is recovered from roots of spontaneous or cultivated *Echinacea angustifolia* by means of a process comprising the following steps:

a) removing non-polysaccharide components from the roots by extraction with solvent;

b) extracting the polysaccharide fraction from the roots as directly obtained from the preceding step;

c) isolating the polysaccharide by chromatography of the polysaccharide fraction.

The purpose of step a) is to remove the non-polysaccharide components of the roots, mainly echinacoside and analogues thereof, as well as the large group of alkylamides which are also characteristic components of *Echinacea angustifolia* (R. Bauer et al., Phytochemistry 28, 505, 1989; Planta Med. 55, 367, 1989). Accordingly, the roots are extracted with a solvent selected from acetone or an alcohol from one to three carbon atoms, optionally in admixture with water, at a temperature ranging from 20° C. to the boiling temperature, preferably under reflux. The water content of the solvent must not exceed 40% (v/v). Ethanol at a concentration between 80 and 95% (v/v) is the preferred solvent.

The purpose of step b) is to extract the mixture of the polysaccharide components from the roots. The extraction is carried out with water, acetone or an alcohol from one to three carbon atoms, in admixture with water, at a temperature ranging from 20° C. to the boiling temperature of the solvent, preferably from 40 to 70° C. When mixtures of solvents are used, the water content will be 60% or higher, preferably 85% (v/v). According to a preferred embodiment of the invention, the solvent is 15% (v/v) ethanol.

Step c) provides the fractioning of the extract from step b) and the separation of the polysaccharide from other polar components of the extract. This step preferably consists in size-exclusion chromatography or ion exchange chromatography.

In the first case, the polysaccharide is purified based on its molecular dimensions: in fact the polysaccharide has a characteristic mass, which is different from that of all the other components. A suitably cross-linked resin can separate chemical species having different dimensions; processing the extract from step b) through a resin of this type (for example Toyopearl HW-65S and Superdex®200HR) allows to purify the polysaccharide of the invention.

The purification of the polysaccharide by ion exchange chromatography is based on the acidic character of the polysaccharide, due to the presence of carboxy functions in the galacturonic acid units. Processing the extract from step b) through an anion exchange resin allows to retain only the polysaccharide and any other acidic components (which are present in small amounts) and to remove all the neutral or basic components. The resin is washed with a saline or acidic aqueous solution to recover the molecules entrapped by the resin. The salts or the acids in the purified solution are thereafter removed by means of ultrafiltration dialysis. A sufficiently high cutoff (e.g. 10,000 or 100,000 Da) is selected to remove also the acidic impurities in the starting extract and retained by the anionic resin.

Preferred anion exchange resins are strong ion exchange resins, such as Diaion HPA 25 and Q Sepharose®Fast Flow.

The polysaccharide purified solution obtained according to one of the cromatographic processes described in step c) is then concentrated and dried under vacuum or freeze-dried. The polysaccharide is an ivory-colour powder.

Step c) can also comprise preliminary purification steps, useful for making the chromatography easier. Even though not indispensable, these steps allow to remove a first aliquot of impurities from the extract of step b) and to reduce the amount of resin.

Preliminary Treatments are Selected From:

c1) concentration of the extract from step b) under reduced pressure and subsequent purification by treatment with a mixture of water and acetone or water and an alcohol from one to three carbon atoms, preferably ethanol. The mixture will contain 50–70%, preferably 66.5%, of alcohol or acetone. According to a preferred embodiment of the invention, the residue resulting from concentration of the extract is dissolved at room temperature with three parts of water and diluted under stirring with 7 volumes of 95% ethanol. The precipitated fraction, which contains the polysaccharide, is collected by filtration, washed with ethanol at a concentration from 50 to 70% and subjected to chromatographic purification.

c2) treatment of the polysaccharide fraction from step b), or of the enriched fraction from step 1c), with water at room temperature. In this way the polysaccharide of the invention, which is highly soluble in water, is separated from other sparingly soluble polysaccharides. The extract resulting from step b) (or the fraction enriched in polysaccharides from step c1)) is suspended in water at room temperature and stirred to promote dissolution. The insoluble residue is separated and the aqueous solution is subjected to chromatography.

c3) enzymatic treatment, useful for hydrolising inulin-like oligosaccharides and polysaccharides, which represent one of the main impurities of the extract from step b). The extract (or one of the partially purified products from steps c1) or c2)) is treated, in aqueous solution, with a catalytic amount of inulinase for 10–24 hours. The enzyme is then heat- or trypsin-inactivated and the carbohydrate fragments formed upon hydrolysis are removed by dialysis (tangential ultrafiltration with cut-off higher than 10,000 Da, preferably 100,000 Da). The retentate thus obtained is then subjected to chromatography.

c4) high cutoff ultrafiltration (cutoff higher than 10,000 Da, preferably 100,000 Da) to remove low molecular weight impurities. In this case, the extract from step b) (or one of the partially purified products from steps c1) or c2)) is dissolved in water, preferably 10 or 20 volumes, and dialysed. The retentate, which contains the polysaccharide of the invention, is then subjected to chromatography.

The polysaccharide of the invention showed immune-stimulating properties in mice, in particular proved able to stimulate T-lymphocytes activation and to counteract the effect of cyclosporin A, thus reducing the mortality due to *Candida albicans* infection. The polysaccharide of the invention can be therefore used for the preparation of medicaments, food supplements or nutraceutical compositions to be administered in situations in which an increase of the immune system body defenses is desirable.

The polysaccharide can be formulated according to conventional techniques, for example according to those described in Remington's Pharmaceutical Sciences Handbook, XVII ed. Mack Pub., N.Y., U.S.A.

The present invention is hereinafter illustrated by means of some examples.

EXAMPLES

In all the following examples, the determination of the polysaccharide HPLC titre is carried out with a TosoHaas TSK-Gel G 5000 PWXL column eluted with water containing 0.5% of triethylamine in isocratic conditions at a flow rate of 0.5 ml/min. During the analysis, which lasts 30 minutes, the column is kept at 50° C. The injection volume is 50 µl. An evaporative detector ELSD (Evaporative Light Scattering Detector) Sedex mod. 75 (S. E. D. E. R. E.) —whose nebulizer is kept at 60° C. with gas pressure of 2.2 bars is coupled to the column.

Example 1
Extraction of *Echinacea angustifolia* Roots (Steps a) and b))

600 grams of ground roots of *Echinacea angustifolia* are extracted under reflux for four hours with 2.5 L of 90% (v/v) ethanol. The percolate is collected and further seven extractions with the same solvent (step a)) are carried out. The resulting extract is discarded. The roots are then extracted seven times at 70° C. with 15% (v/v) ethanol, each extraction lasting four hours. The combined percolates are filtered and concentrated under vacuum, affording 170 g of brown residue (whole polysaccharides extract, step b)).

Example 2
Recovery of the Polysaccharide by Pre-Purification with Solvents and Anion Exchange Chromatography 170 g of the whole polysaccharides extract from step b) of example 1 are dissolved in 570 ml of water and 1.13 L of ethanol are then added. The mixture is stirred for about one hour, the precipitate is decanted for about 20 minutes, filtered, washed with 850 ml of 66.5% (v/v) ethanol and dried at 55° C. under vacuum for 48 hours, affording 140 g of a hazel-color solid. The solid is taken up with 2.1 L of water and the resulting suspension is left under stirring for 20 minutes, then separated from the insoluble residue (which is discarded).

The aqueous solution, enriched in the polysaccharide of the invention, gives a dry residue of 38.7 g. The solution is loaded on a chromatographic column containing 0.9 L of Diaion HPA 25 resin conditioned with $AcOH/AcNH_4$ buffer at pH 6.1. The resin is washed with 5.4 L of $AcOH/AcNH_4$ buffer solution at pH 6.1, and the fraction containing the polysaccharide is eluted with 5.4 L of a 0.5 M $AcNH_4$ aqueous solution. The eluate is concentrated to 0.3 L under reduced pressure. The concentrated solution is subjected to dialysis by tangential ultrafiltration with 6 L of purified water, using a 10,000 Da cutoff spiral-wound membrane in polyethersulfone.

The retentate is recovered and concentrated under reduced pressure and the residue is heat-dried under vacuum, affording 7.1 g of an ivory-color powder (polysaccharide HPLC titre: 96%).

The polysaccharide has average molecular weight of $1.3 \times 10^5$ Da (s=5365), with <Mn 14320 (s=2180), which is consistent with a determination by means of LALLS (Low Angle Laser Light Scattering) and consists of galacturonic acid, galactose, arabinose and rhamnose in 10.25:1.75:2.5:0.5 ratio (HPAEC analysis). The polysaccharide has characteristic $^1H$-NMR, $^{13}C$-NMR spectra and GPC profile, as reported in FIGS. 1–3 respectively.

Example 3
Recovery of the Polysaccharide by Ultrafiltration Pre-purification and Size-exclusion Chromatography 170 g of the whole polysaccharides extract from step b) of example 1 are dissolved in 850 ml of purified water. The solution is dialysed by tangential ultrafiltration with 10 L of purified water, using a 50,000 Da cutoff spiral-wound membrane in polyethersulfone.

The retentate, which contains 110.5 g of purified extract, is recovered and loaded on a chromatographic column kept under medium pressure and containing 22 L of Toyopearl HW-65S resin conditioned with water. The elution is carried out with purified water, dividing the eluates in fractions 200 ml each. The fractions are GPC-analyzed and those containing sufficiently pure polysaccharide are pooled.

The pooled fractions are then concentrated under reduced pressure and the residue is heat-dried under vacuum, affording 5.7 g of ivory-color powder (polysaccharide HPLC titre: 95%).

Example 4
Recovery of the Polysaccharide by Enzymatic Pre-purification and Anion Exchange Chromatography 170 g of the whole polysaccharides extract from step b) of example 1 are dissolved in 3230 ml of purified water and 850 mg of enzyme inulinase are added. The mixture is left under gentle stirring at 40° C. for 24 hours, then the enzyme is inactivated with 80 mg of trypsin, stirring for 2 hours at 36° C. The solution is heated at 85° C. for 2 hours and concentrated under reduced pressure to 1.7 L.

The concentrated solution is subjected to dialysis by tangential ultrafiltration with 17 L of purified water, using a 100,000 Da cutoff spiral-wound membrane in polyethersulfone. The retentate (which contains 11.5 g of purified extract) is recovered and loaded on a chromatographic column containing 0.8 L of Diaion HPA 25 resin conditioned with $AcOH/AcNH_4$ buffer at pH 6.1. The resin is washed with 4.8 L of $AcOH/AcNH_4$ buffer solution at pH 6.1, and the fraction containing the polysaccharide is eluted with 4.8 L of a 0.5 M $AcNH_4$ aqueous solution. The eluate is concentrated to 150 ml under reduced pressure and the concentrate is dialysed by tangential ultrafiltration with 1.5 L of purified water, using a 50,000 Da cutoff spiral-wound membrane in polyethersulfone.

The retentate is concentrated under reduced pressure and the residue is heat-dried under vacuum, obtaining 6.9 g ivory-color powder (polysaccharide HPLC titre: 97%).

BIOLOGICAL SECTION

Experiment 1

Test for the Production of γ-interferon in T-lymphocytes (Zucca M. et al, New Microbiol. 1996, 19, 39–46)

Murine T-lymphocytes obtained by separation of splenocites on nylon-wool column, were cultured in 1640 RPMI medium with 4% of fetal calf serum in microtitre plates optionally pre-incubated with α-CD3 (anti-CD3 monoclonal antibody as cell function activator responsible for interferon production). The substances to test were added to the wells and after 48 hours γ-interferon released in the incubation medium was evaluated.

TABLE 1

| TREATMENT | γ-Interferon pg/ml |
| --- | --- |
| Medium | 4.5 ± 0.5 |
| α-CD3 | 149.5 ± 25.0 |
| α-CD3 + Polysaccharide 0.1 µg/ml | 410.0 ± 45.7 |
| α-CD3 + Polysaccharide 1.0 µg/ml | 466.3 ± 71.8 |
| α-CD3 + Polysaccharide 10.0 µg/ml | 690.5 ± 95.5 |

Experiment 2

Effect on Mortality Induced by *Candida Albicans* in Mice (Microbiology, 2000, 146,1881–9)

Yeasts were cultured in Sabouraud agarized medium and intravenously inoculated at a concentration of $2.9 \times 10^5$ in mice immune-suppressed with 1 mg/Kg i.p. of cyclosporin A (CsA). Mice were treated daily with 5 and 10 mg/Kg i.p. of the polysaccharide of the invention until death of all the control mice (untreated). The results were evaluated as survived animals in the treated groups.

TABLE 2

| TREATMENT | % OF SURVIVED ANIMALS |
| --- | --- |
| *Candida albicans* (CA) + CsA | 0 |
| CA + CsA + polysaccharide 5 mg/kg | 30 |
| Ca + CsA + polysaccharide 10 mg/Kg | 50 |

We claim:

1. A polysaccharide of *Echinacea angustifolia* roots having molecular weight of $1.3 \times 10^5$ Da and consisting of rhamnose, arabinose, galactose and galacturonic acid in 0.5:2.5:1.75:10.25 ratio.

2. The polysaccharide according to claim 1 characterized by a skeleton with alternate straight and branched portions, the straight portions consisting of partially acetylated and methylated galacturonic acid residues linked via α-(1–4) bond and the branched portions consisting of an alternation of galacturonic acid and rhamnose, to which side chains containing arabinose and galactose in 2.5;1.75 ratio are attached.

3. A process for the preparation of the polysaccharide of claim 1 comprising the following steps:
   a) removing non-polysaccharide components from the roots extraction with solvent;
   b) extracting with solvent the polysaccharide fraction from the roots as directly obtained from the preceding step;
   c) isolating the polysaccharide by chromatography of the polysaccharide fraction.

4. The process according to claim 3 wherein the solvent used in step a) is acetone or an alcohol having one to three carbon atoms.

5. The process according to claim 4 wherein the solvent is in admixture with water.

6. The process according to claim 5 wherein the water content of the solvent is not higher than 40%.

7. The process according to claim 4 wherein the solvent is ethanol with a concentration ranging from 80 to 95%.

8. The process according to claim 4 wherein the extraction temperature ranges from 20° C. to the boiling temperature of the solvent.

9. The process according to claim 3 wherein the solvent used in step b) is water or a mixture of water and acetone or water and an alcohol having one to three carbon atoms.

10. The process according to claim 9 wherein the water content of the solvent mixture is 60% or higher.

11. The process according to claim 9 wherein the solvent is 15% ethanol.

12. The process according to claim 9 wherein the extraction is carried out at a temperature ranging from 20° C. to the boiling temperature of the solvent.

13. The process according to claim 3 wherein the chromatography of step c) is a size-exclusion chromatography or an ion-exchange chromatography.

14. The process according to claim 3 wherein, before chromatography of step c), the polysaccharide fraction from step b) is subjected to one or more preliminary purification treatments.

15. The process according to claim 14 wherein preliminary purification treatments are selected from:
   1) precipitation and isolation of a polysaccharides-enriched fraction by dissolution in a mixture of water and 50–70% of acetone or water and 50–70% of an alcohol having one to three carbon atoms;
   2) removal of the insoluble polysaccharide fraction by treatment with water;
   3) treatment with inulinase;
   4) ultrafiltration with cutoff 10,000 Da or higher.

16. The process according to claim 15 wherein preliminary purification treatments 1) and 2) are carried out.

17. The process according to claim 15 wherein preliminary purification treatment 3), optionally preceeded by one or both purification treatments 1) and 2), is carried out.

18. The process according to claim 15 wherein preliminary purification treatment 4), optionally preceeded by one or both purification treatments 1) and 2), is carried out.

19. A medicament comprising the polysaccharide of claim 1.

20. Pharmaceutical and nutraceutical compositions and food supplements containing the polysaccharide of claim 1.

* * * * *